US011400034B2

(12) United States Patent
Page et al.

(10) Patent No.: US 11,400,034 B2
(45) Date of Patent: Aug. 2, 2022

(54) COSMETIC COMPOSITION COMPRISING ONE OR MORE POLAR OIL(S), A $C_2$—$C_6$ ALIPHATIC MONOALCOHOL AND A POLYOL, AT LEAST ONE HYDROPHILIC ACTIVE AGENT, AND COMPRISING LESS THAN 7% BY WEIGHT OF WATER

(71) Applicant: L'OREAL, Paris (FR)

(72) Inventors: Valérie Page, Gigors et Lozeron (FR); Céline Demarcq, Gigors et Lozeron (FR)

(73) Assignee: L'OREAL, Paris (FR)

( * ) Notice: Subject to any disclaimer, the term of this patent is extended or adjusted under 35 U.S.C. 154(b) by 0 days.

(21) Appl. No.: 16/470,734

(22) PCT Filed: Dec. 18, 2017

(86) PCT No.: PCT/EP2017/083387
§ 371 (c)(1),
(2) Date: Jun. 18, 2019

(87) PCT Pub. No.: WO2018/114850
PCT Pub. Date: Jun. 28, 2018

(65) Prior Publication Data
US 2019/0336420 A1    Nov. 7, 2019

(30) Foreign Application Priority Data
Dec. 22, 2016    (FR) ...................................... 1663266

(51) Int. Cl.
| | | |
|---|---|---|
| *A61K 8/34* | (2006.01) | |
| *A61K 8/368* | (2006.01) | |
| *A61K 8/60* | (2006.01) | |
| *A61Q 19/00* | (2006.01) | |
| *A61Q 19/08* | (2006.01) | |

(52) U.S. Cl.
CPC ................ *A61K 8/34* (2013.01); *A61K 8/345* (2013.01); *A61K 8/368* (2013.01); *A61K 8/602* (2013.01); *A61Q 19/00* (2013.01); *A61Q 19/007* (2013.01); *A61Q 19/08* (2013.01)

(58) Field of Classification Search
None
See application file for complete search history.

(56) References Cited

U.S. PATENT DOCUMENTS

| | | | |
|---|---|---|---|
| 2004/0076652 A1 | 4/2004 | Paspaleeva-Kuhn et al. | |
| 2008/0008674 A1 | 1/2008 | Burnier et al. | |
| 2010/0168055 A1 | 7/2010 | Laboureau et al. | |
| 2011/0217253 A1* | 9/2011 | Arnaud .................. | A61K 8/064 424/63 |

FOREIGN PATENT DOCUMENTS

| | | | |
|---|---|---|---|
| CN | 101277673 A | 10/2008 | |
| CN | 101484128 A | 7/2009 | |
| EP | 0 507 691 A1 | 10/1992 | |
| EP | 2 295 114 A1 | 3/2011 | |
| FR | 2903008 A1 * | 1/2008 | ............... A61K 8/60 |
| FR | 2 924 602 A1 | 6/2009 | |
| FR | 2 939 679 A1 | 6/2010 | |
| FR | 2 954 126 A1 | 6/2011 | |
| FR | 3 005 857 A1 | 11/2014 | |
| JP | 2004-525877 A | 8/2004 | |
| JP | 2008 013561 A | 1/2008 | |
| JP | 2009-504583 A | 2/2009 | |
| JP | 2010 155836 A | 7/2010 | |
| WO | WO 02/051828 A2 | 7/2002 | |
| WO | WO 2004/016289 A1 | 2/2004 | |
| WO | WO 2007/017119 A2 | 2/2007 | |
| WO | WO 2008/020140 A1 | 2/2008 | |
| WO | WO 2011/029516 A2 | 3/2011 | |
| WO | WO 2013/093823 A2 | 6/2013 | |

OTHER PUBLICATIONS

Kosugi, "Liquid emulsifiable bathing agent", JPN. Tokkyo Koho, Oct. 3, 1975, XP002774177.
"Personal care compositions proving high UVA/UVB light protection and radical scavenging effect", ip.com Journal, May 5, 2009, pp. 1-121, XP013131429.

* cited by examiner

*Primary Examiner* — Dale R Miller
(74) *Attorney, Agent, or Firm* — Polsinelli PC

(57) ABSTRACT

A subject of the invention is a cosmetic composition comprising: —from 30% to 89% by weight of at least one polar oil relative to the total weight of the composition; —from 10% to 45% by weight of at least one $C_2$-$C_6$ aliphatic monoalcohol relative to the total weight of the composition; —from 0.5% to 50% by weight of at least one polyol relative to the total weight of the composition; —at least one hydrophilic active agent, said composition comprising less than 7% by weight of water relative to the total weight of the composition. It also relates to the associated cosmetic process and also the cosmetic use of said composition.

16 Claims, No Drawings

COSMETIC COMPOSITION COMPRISING ONE OR MORE POLAR OIL(S), A $C_2$—$C_6$ ALIPHATIC MONOALCOHOL AND A POLYOL, AT LEAST ONE HYDROPHILIC ACTIVE AGENT, AND COMPRISING LESS THAN 7% BY WEIGHT OF WATER

CROSS REFERENCE TO RELATED APPLICATIONS

This application is a National Phase filing under 35 U.S.C. § 371 of PCT/EP2017/083387 filed on Dec. 18, 2017; which application in turn claims priority to Application No. 1663266 filed in France on Dec. 22, 2016. The entire contents of each application are hereby incorporated by reference.

The invention relates to a cosmetic composition comprising from 30% to 89% by weight of at least one polar oil, from 10% to 45% by weight of at least one $C_2$-$C_6$ aliphatic monoalcohol, and from 0.5% to 50% by weight of at least one polyol relative to the total weight of the composition, and at least one hydrophilic active agent, said composition comprising less than 7% by weight of water.

The invention also relates to a process for the cosmetic treatment of keratin materials, in particular of the skin of the face and/or of the body, comprising the application of said composition to said keratin materials.

Moreover, the invention also relates to the use of said composition for the cosmetic treatment of keratin materials, in particular for caring for and/or making up said keratin materials, such as the skin of the body and/or face.

In the cosmetic field of care, cosmetic compositions making it possible to obtain both good sensory properties and also a care effect are increasingly sought-after by users. Care effect is intended to mean, for example, an effect against the dryness or ageing of the keratin materials and especially the skin, this care effect being provided by active agents.

To this end, hydrophilic active agents, for example C-glycosides, prove particularly beneficial; in particular, these compounds have particularly good performance in treating problems of skin ageing.

In addition, oily presentation forms are particularly beneficial for improving the delivery of an active agent during application to the keratin materials, preferably the skin, and hence the effectiveness thereof, in particular the effectiveness thereof in treating problems of skin ageing. Oily presentation forms are also increasingly sought-after in the field of cosmetics and more particularly in the field of skincare, especially since they make it possible to provide nutrition and a silky finish after application.

However, obtaining this dual effect (good sensory properties and care effect) firstly requires being able to introduce one (or more) hydrophilic active agent(s) in a sufficient amount into the composition; thus, the hydrophilic nature of this (these) active agent(s) makes it difficult to incorporate these compounds into oily presentation forms comprising less than 7% by weight of water; it also requires overcoming the drawbacks associated with oily presentation forms, in particular sensory drawbacks and drawbacks in terms of ease of use; these presentation forms especially tend to leave a greasy, shiny finish after application, and have a slow penetration speed during application.

Consequently, there therefore remains a need for cosmetic compositions which are rich in oil(s), in particular rich in oil(s) of natural origin, and comprising also an effective amount of hydrophilic active agent(s) making it possible to improve the delivery of these active agents during application to keratin materials, preferably the skin, which are stable, and have good sensory properties, especially having more rapid penetration and/or a fresh effect on application, and a less greasy, less shiny, less film-forming and/or less tacky finish after application while retaining the beneficial properties of the oils, in particular nutrition, smoothness on application, and a silky finish on the skin.

"Penetration speed" is intended to mean the speed at which the composition penetrates into the keratin materials, preferably the skin, corresponding to the massage time necessary for the penetration of the composition.

"Fresh effect on application" is intended to mean the ability of a composition to provide a sensation of freshness during the application thereof to keratin materials, especially to the skin.

"Less greasy finish" is intended to mean a finish, after application to keratin materials, preferably the skin, which leaves fewer greasy-buttery residues, as well as on the fingers which applied the composition.

"Less shiny finish" is intended to mean a finish, after application to keratin materials, in particular the skin, which is less shiny when the skin reflects the light.

"Less tacky finish" is intended to mean a finish, after application to keratin materials, preferably the skin, which has less adhesion when the skin is tapped with the fingers.

"Silky finish" is intended to mean a sensation of comfort and softness after application of the composition to keratin materials, preferably the skin.

"Rich in oil" is intended to mean a composition comprising more than 30% of oil(s).

An oil is said to be "of natural origin" when the latter was not produced synthetically or when the latter is not derived from petrochemicals.

The applicant has observed, surprisingly, that a cosmetic composition comprising from 30% to 89% by weight of at least one polar oil, from 10% to 45% by weight of at least one $C_2$-$C_6$ aliphatic monoalcohol and from 0.5% to 50% by weight of at least one polyol, and at least one hydrophilic active agent, said composition comprising less than 7% by weight of water, makes it possible to obtain better penetration of the composition and especially better delivery of the hydrophilic active agent(s) during application to keratin materials, preferably the skin.

In addition, the composition according to the invention makes it possible to obtain good sensory properties, especially having more rapid penetration and/or a fresh effect on application and a less greasy, less shiny, less film-forming and/or less tacky finish after application while retaining the beneficial properties of the oils, in particular nutrition, smoothness on application and a silky finish on the skin.

The composition according to the invention also has good stability properties.

A composition is said to be stable when no, or virtually no, change in its macroscopic appearance (clarity, homogeneity, fluidity) and in its physicochemical characteristics (viscosity) is observed after being conserved at a temperature of 4° C. and 45° C. for a duration of one month, preferably 2 months and/or after a cyclic study, in particular after 10 cycles of 24 h, one cycle corresponding to conservation of the composition for 6 h at 20° C., then 6 h decreasing down to −20° C., then 6 h at −20° C., and finally 6 h rising back up to 20° C.

In particular, the composition according to the invention also has a clear, homogeneous and fluid appearance.

For the purposes of the present invention, "clear" is intended to mean a composition having a transparent appearance.

For the purposes of the present invention, "homogeneous" is intended to mean a composition consisting of a single phase.

For the purposes of the present invention, "fluid" is intended to mean a composition which flows easily under the effect of its own weight.

Thus, one subject of the present invention is a cosmetic composition comprising:
 from 30% to 89% by weight of at least one polar oil relative to the total weight of the composition;
 from 10% to 45% by weight of at least one $C_2$-$C_6$ aliphatic monoalcohol relative to the total weight of the composition;
 from 0.5% to 50% by weight of at least one polyol relative to the total weight of the composition;
 and at least one hydrophilic active agent,
said composition comprising less than 7% by weight of water relative to the total weight of the composition.

In a particular embodiment, the composition according to the invention is intended for topical application, especially to keratin materials.

It especially comprises a physiologically acceptable medium, that is to say a medium compatible with all the keratin materials, in particular the skin.

For the purposes of the present invention, "keratin materials" is intended to mean the skin and skin appendages.

"Skin" is intended to mean facial and/or bodily skin and the scalp.

"Skin appendages" is intended to mean the eyelashes, the eyebrows, the nails and the hair, in particular the eyelashes and the hair.

According to another particular embodiment of the invention, the composition is intended for topical administration to keratin materials such as the skin of the face and/or the body.

The present invention also relates to a process for the cosmetic treatment of keratin materials, characterized in that a composition in accordance with the present invention is applied to said keratin materials.

Moreover, another subject of the invention is the use of said composition in the field of cosmetics, in particular for caring for the skin of the body or of the face.

According to a particular embodiment, the composition according to the invention also comprises less than 5% by weight of surfactant, preferably less than 3% by weight of surfactant, even more preferentially less than 2% by weight of surfactant relative to the total weight of the composition. According to a particular embodiment, the composition according to the invention comprises less than 1% by weight of surfactant relative to the total weight of the composition, or even the composition is free from surfactant.

For the purposes of the present invention, "surfactant" is intended to mean an amphiphilic molecule, i.e. it has two parts of different polarity, one generally being lipophilic (soluble or dispersible in an oily phase), and the other being hydrophilic (soluble or dispersible in water). Surfactants are characterized by their HLB (hydrophilic-lipophilic balance) value, the HLB being the ratio between the hydrophilic part and the lipophilic part in the molecule. The term "HLB" is well known to those skilled in the art and is described, for example, in "The HLB system. A time-saving guide to Emulsifier Selection" (published by ICI Americas Inc., 1984). For emulsifying surfactants, the HLB generally ranges from 3 to 8 for the preparation of W/O emulsions and from 8 to 18 for the preparation of O/W emulsions. The HLB of the surfactant(s) used according to the invention may be determined via the Griffin method or the Davies method. In a particular embodiment, the composition according to the invention does not comprise emulsifying surfactants such as polyoxyethylenated castor oil, oxyethylenated or non-oxyethylenated esters of fatty acid and of sorbitol and/or of sorbitan, such as polysorbates, phospholipids, esters of polyethylene glycol and of fatty acid such as PEG-15 stearate, and also lecithin.

The composition according to the invention comprises less than 7% by weight of water relative to the total weight of the composition, preferably less than 6% by weight of water relative to the total weight of the composition. Preferably, the composition according to the invention comprises from 4% to 5% by weight of water relative to the total weight of the composition.

In a first particular embodiment, the composition according to the invention comprises from 3% to 4% by weight of water relative to the total weight of the composition.

In a second particular embodiment, the composition according to the invention comprises from 0% to 1% by weight of water relative to the total weight of the composition, or even the composition is free from water.

Preferably, the composition according to the invention has a viscosity of less than 1.07 Pa.s, preferably less than 0.73 Pa.s.

The viscosity is measured at 25° C., using a Rheomat RM 180 viscometer equipped with a No. 1 spindle, the measurement being carried out after 10 minutes of rotation of the spindle in the composition (after which time stabilization of the viscosity and of the speed of rotation of the spindle are observed), at a shear rate of 200 $s^{-1}$.

The composition according to the invention differs from emulsions especially in that it is not in the form of a dispersion of two liquids which are immiscible with one another at room temperature (20-25° C.). Indeed, the composition according to the invention does not have a dispersed phase (also referred to as discontinuous phase) in the form of droplets in a dispersing phase (also referred to as continuous phase). Macroscopic analysis (with the naked eye) of the composition according to the invention shows a clear, transparent and single-phase appearance.

In the following text, the expression "at least one" is equivalent to "one or more" and, unless indicated otherwise, the limits of a range of values are included within that range.

Polar Oil

The composition according to the invention comprises from 30% to 89% by weight of at least one polar oil relative to the total weight of the composition. Preferably, the composition according to the invention comprises from 40% to 60% by weight of at least one polar oil, from 45% to 56% by weight of at least one polar oil relative to the total weight of the composition.

The term "oil" is intended to mean any fatty substance that is in liquid form at room temperature (25° C.) and at atmospheric pressure.

Among the oils which may be used in the present invention, mention may be made of: volatile or non-volatile oils; these oils may be hydrocarbon-based oils, especially of animal or plant origin, synthetic oils, silicone oils, fluoro oils, or mixtures thereof.

For the purposes of the present invention, "silicone oil" is intended to mean an oil comprising at least one silicon atom, and especially at least one Si—O group.

"Hydrocarbon-based oil" is intended to mean an oil mainly containing hydrogen and carbon atoms and optionally oxygen, nitrogen, sulfur and/or phosphorus atoms.

For the purposes of the present invention, "polar oil" is intended to mean an oil of which the solubility parameter $\delta_n$ at 25° C. is other than 0 $(J/cm^3)^{1/2}$. In particular, "polar oil" is intended to mean an oil of which the chemical structure is formed essentially from, or even constituted of, carbon and hydrogen atoms, and comprising at least one highly electronegative heteroatom such as an oxygen, nitrogen, silicon or phosphorus atom.

The definition and calculation of the solubility parameters in the Hansen three-dimensional solubility space are described in the article by C. M. Hansen: *The three-dimensional solubility parameters,* J. Paint Technol., 39, 105 (1967).

According to this Hansen space:
$\delta_D$ characterizes the London dispersion forces resulting from the formation of dipoles induced during molecular impacts;
$\delta_p$ characterizes the Debye interaction forces between permanent dipoles and also the Keesom interaction forces between induced dipoles and permanent dipoles;
$\delta_h$ characterizes the forces of specific interactions (such as hydrogen bonds, acid/base bonds, donor/acceptor bonds, and the like);
$\delta_n$ is determined by the equation: $\delta_n = (\delta_p^2 + \delta_h^2)^{1/2}$.

The parameters $\delta_p$, $\delta_h$, $\delta_D$ and $\delta_a$ are expressed as $(J/cm^3)^{1/2}$.

Preferably, the polar oils used according to the present invention have a $\delta_a$ of between 4 and 9.1, preferably a $\delta_a$ of between 6 and 9.1, even better still between 7.3 and 9.1.

Non-Volatile Polar Oils

For the purposes of the present invention, "non-volatile oil" is intended to mean an oil having a vapour pressure of less than 0.13 Pa (0.01 mmHg).

The non-volatile oils may be chosen especially from non-volatile hydrocarbon-based oils, which may be fluorinated, and/or non-volatile silicone oils.

As non-volatile hydrocarbon-based oils that are suitable for use in the invention, mention may be made especially of:
hydrocarbon-based oils of animal origin,
hydrocarbon-based oils of plant origin such as phytostearyl esters, such as phytostearyl oleate, phytostearyl isostearate and lauroyl/octyldodecyl/phytostearyl glutamate, for example sold under the name Eldew PS203® by Ajinomoto, triglycerides constituted of fatty acid esters of glycerol, the fatty acids of which may have chain lengths ranging from $C_4$ to $C_{24}$, these chains possibly being linear or branched, and saturated or unsaturated; these oils are especially heptanoic or octanoic triglycerides, wheatgerm oil, sunflower oil, grapeseed oil, sesame oil, corn oil, apricot oil, castor oil, camelina oil, shea oil, avocado oil, olive oil, soybean oil, sweet almond oil, palm oil, rapeseed oil, cotton seed oil, hazelnut oil, macadamia oil, jojoba oil, alfalfa oil, poppy oil, pumpkin oil, marrow oil, blackcurrant oil, evening primrose oil, millet oil, barley oil, quinoa oil, rye oil, safflower oil, candlenut oil, passion flower oil or musk rose oil; shea butter; or alternatively caprylic/capric acid triglycerides, for instance those sold by Stéarineries Dubois or those sold under the names Miglyol 810®, 812® and 818® by Dynamit Nobel; the refined vegetable perhydrosqualene sold under the name Fitoderm by Cognis.

As example of castor oil according to the invention, mention may more particularly be made of castor oil comprising at least 50% by weight of linear or branched, saturated or unsaturated $C_{14}$-$C_{22}$ fatty acids, preferably at least 70% by weight of linear or branched, saturated or unsaturated $C_{16}$-$C_{20}$ fatty acids, even better still at least 50% by weight of linear or branched, saturated or unsaturated $C_{18}$ fatty acids, including less than 5% by weight of saturated $C_{18}$ fatty acids, preferably less than 2.5% by weight of saturated $C_{18}$ fatty acids such as stearic acid, 50% to 98% by weight of monounsaturated $C_{18}$ fatty acids, even more preferentially 80% to 98% by weight of monounsaturated $C_{18}$ fatty acids, such as ricinoleic and oleic acids, less than 10% by weight of polyunsaturated $C_{18}$ fatty acids, preferably from 2% to 8% of polyunsaturated $C_{18}$ fatty acids such as linoleic and linolenic acids, relative to the total weight of fatty acids present in said castor oil; such a castor oil is sold by Vertellus under the name Crystal O.

As example of camelina oil according to the invention, mention may more specifically be made of camelina oil comprising at least 50% by weight of linear or branched, saturated or unsaturated $C_{14}$-$C_{22}$ fatty acids, preferably at least 70% by weight of linear or branched, saturated or unsaturated $C_{16}$-$C_{20}$ fatty acids, even better still at least 50% by weight of linear or branched, saturated or unsaturated $C_{18}$ fatty acids, including less than 5% by weight of saturated $C_{18}$ fatty acids such as stearic acid, 12% to 26% by weight of monounsaturated $C_{18}$ fatty acids, such as oleic acid, from 35% to 64% by weight of polyunsaturated $C_{18}$ fatty acids, such as linoleic and linolenic acids, relative to the total weight of fatty acids present in said camelina oil; such a camelina oil is sold by Greentech under the name Camelina Refined Oil C05002.

As examples of caprylic/capric acid triglycerides, mention may be made of those comprising from 45% to 80% by weight of $C_8$ fatty acids and from 20% to 45% by weight of $C_{10}$ fatty acids, and especially those sold by PT MUSIM MAS.

synthetic esters, such as the oils of formula $R_1COOR_2$, in which $R_1$ represents the residue of a linear or branched fatty acid comprising from 1 to 40 carbon atoms and $R_2$ represents an especially branched hydrocarbon-based chain containing from 1 to 40 carbon atoms, with the proviso that $R_1+R_2$ is ≥10.

The esters may be chosen especially from fatty acid esters, for instance:
cetostearyl octanoate, esters of isopropyl alcohol and of C8-C18, preferably C12-C16 fatty acids, such as isopropyl myristate, isopropyl palmitate, ethyl palmitate, 2-ethylhexyl palmitate, isopropyl stearate, isopropyl isostearate, isostearyl isostearate, octyl stearate, hydroxylated esters, for instance isostearyl lactate, octyl hydroxystearate, diisopropyl adipate, heptanoates, and especially isostearyl heptanoate, alcohol or polyalcohol octanoates, decanoates or ricinoleates, for instance propylene glycol dioctanoate, cetyl octanoate, tridecyl octanoate, 2-ethylhexyl 4-diheptanoate, 2-ethylhexyl palmitate, alkyl benzoate, polyethylene glycol diheptanoate, propylene glycol 2-diethylhexanoate, and mixtures thereof, $C_{12}$ to $C_{15}$ alcohol benzoates, hexyl laurate, neopentanoic acid esters, for instance isodecyl neopentanoate, isotridecyl neopentanoate, isostearyl neopentanoate, octyldodecyl neopentanoate, isononanoic acid esters, for instance isononyl isononanoate, isotridecyl isononanoate, octyl isononanoate, hydroxylated esters, for instance isostearyl lactate and diisostearyl malate;
polyol esters and pentaerythrityl esters, for instance dipentaerythrityl tetrahydroxystearate/tetraisostearate;

esters of diol dimers and of diacid dimers, such as Lusplan DD-DA5® and Lusplan DD-DA7® sold by Nippon Fine Chemical and described in patent application FR 0302809, fatty alcohols that are liquid at room temperature, with a branched and/or unsaturated carbon-based chain having from 12 to 26 carbon atoms, preferably 6 to 22 carbon atoms, even better still from 18 to 20 carbon atoms, such as 2-octyldodecanol, isostearyl alcohol, oleyl alcohol, 2-hexyldecanol, 2-butyloctanol and 2-undecylpentadecanol, higher fatty acids such as oleic acid, linoleic acid and linolenic acid, and mixtures thereof; and dialkyl carbonates, the two alkyl chains possibly being identical or different, such as the dicaprylyl carbonate sold under the name Cetiol CC® by Cognis, diesters of C2-C16, preferably C8-C12 dicarboxylic acid and of C1-C4 monoalcohol, preferably of branched C3-C4 monoalcohol. Preferably, the diester of sebacic acid and of isopropyl alcohol, such as the diisopropyl sebacate sold under the name DUB DIS by STEARINERIES DUBOIS, non-volatile silicone oils, such as, for example, non-volatile polydimethylsiloxanes (PDMSs), polydimethylsiloxanes comprising alkyl or alkoxy groups that are pendent and/or at the end of a silicone chain, these groups each containing from 2 to 24 carbon atoms, phenyl silicones, such as phenyl trimethicones, phenyl dimethicones, phenyltrimethylsiloxydiphenylsiloxanes, diphenyl dimethicones, diphenylmethyldiphenyltrisiloxanes and 2-phenylethyltrimethylsiloxysilicates, and dimethicones or phenyl trimethicones with a viscosity of less than or equal to 100 cSt, and mixtures thereof, and mixtures thereof.

Volatile Polar Oils

For the purposes of the present invention, "volatile oil" is intended to mean an oil (or non-aqueous medium) that is capable of evaporating on contact with the skin in less than one hour, at ambient temperature and at atmospheric pressure. The volatile oil is a volatile cosmetic oil, which is liquid at room temperature, especially having a non-zero vapour pressure, at room temperature and atmospheric pressure, in particular having a vapour pressure ranging from 0.13 Pa to 40 000 Pa ($10^{-3}$ to 300 mmHg), in particular ranging from 1.3 Pa to 13 000 Pa (0.01 to 100 mmHg) and more particularly ranging from 1.3 Pa to 1300 Pa (0.01 to 10 mmHg).

Volatile oils that may also be used include volatile silicones, such as, for example, volatile linear or cyclic silicone oils, especially those having a viscosity ≤8 centistokes ($8 \times 10^{-6}$ m$^2$/s), and especially having from 2 to 10 silicon atoms and in particular from 2 to 7 silicon atoms, these silicones optionally comprising alkyl or alkoxy groups having from 1 to 10 carbon atoms. As volatile silicone oils that may be used in the invention, mention may be made especially of dimethicones with a viscosity of 5 and 6 cSt, octamethylcyclotetrasiloxane, decamethylcyclopentasiloxane, dodecamethylcyclohexasiloxane, heptamethylhexyltrisiloxane, heptamethyloctyltrisiloxane, hexamethyldisiloxane, octamethyltrisiloxane, decamethyltetrasiloxane and dodecamethylpentasiloxane, and mixtures thereof.

Volatile fluoro oils such as nonafluoromethoxybutane or perfluoromethylcyclopentane, and mixtures thereof, may also be used. It is also possible to use a mixture of the oils mentioned above.

According to a preferred embodiment, the polar oil(s) is (are) chosen from hydrocarbon-based oils of plant origin, synthetic esters of formula $R_1COOR_2$ in which $R_1$ represents the residue of a linear or branched fatty acid comprising from 1 to 40 carbon atoms and $R_2$ represents a hydrocarbon-based chain, especially branched, containing from 1 to 40 carbon atoms, with the proviso that $R_1+R_2$ is ≥10, fatty alcohols which are liquid at room temperature and contain a branched and/or unsaturated carbon-based chain having from 12 to 26 carbon atoms, dialkyl carbonates, diesters of $C_2$-$C_{16}$ dicarboxylic acid and of $C_1$-$C_4$ monoalcohol; and mixtures thereof.

Preferably, the polar oil(s) is (are) chosen from triglycerides constituted of esters of glycerol and of linear or branched, saturated or unsaturated $C_4$ to $C_{24}$ fatty acids; esters of isopropyl alcohol and of $C_8$-$C_{18}$, preferably $C_{12}$-$C_{16}$, fatty acid; fatty alcohols which are liquid at room temperature and contain a branched and/or unsaturated carbon-based chain having from 16 to 22 carbon atoms, preferably from 18 to 20 carbon atoms; dialkyl carbonates, the two alkyl chains being identical, preferably dicaprylyl carbonate; diesters of $C_8$-$C_{12}$ dicarboxylic acid and of branched $C_3$-$C_4$ monoalcohol, preferably diisopropyl sebacate; and mixtures thereof.

The polar oil(s) within the context of the present invention may preferably be chosen from triglycerides constituted of esters of glycerol and of linear or branched, saturated or unsaturated $C_4$ to $C_{24}$ fatty acids; esters of isopropyl alcohol and of $C_8$-$C_{18}$ fatty acid, fatty alcohols which are liquid at room temperature and contain a branched and/or unsaturated carbon-based chain having from 16 to 22 carbon atoms, and mixtures thereof.

The polar oil(s) within the context of the present invention may preferably be chosen from triglycerides of glycerol and of $C_6$-$C_{12}$ fatty acids, triglycerides of glycerol and of $C_{14}$-$C_{22}$ fatty acids, esters of isopropyl alcohol and of $C_8$-$C_{18}$ fatty acids, fatty alcohols which are liquid at room temperature and contain a branched and/or unsaturated carbon-based chain having from 18 to 20 carbon atoms, and mixtures thereof.

Preferentially, the triglycerides of glycerol and of $C_{14}$-$C_{22}$ fatty acids comprise from 50% to 100% by weight of linear, branched, saturated or unsaturated $C_{18}$ fatty acids, including 0 to 5% by weight of saturated $C_{18}$ fatty acids such as stearic acid, from 50% to 98% by weight of monounsaturated fatty acids such as ricinoleic and/or oleic acids, and/or from 2% to 70% by weight of polyunsaturated $C_{18}$ fatty acids such as linoleic and/or linolenic acids, relative to the total weight of fatty acids contained within said triglycerides.

Preferably, the triglycerides of glycerol and of $C_6$-$C_{12}$ fatty acids comprise from 45% to 80% by weight of $C_8$ fatty acids and from 20% to 45% by weight of $C_{10}$ fatty acids, relative to the total weight of fatty acids contained within said triglycerides.

In a first embodiment, the composition according to the invention comprises at least one polar oil chosen from fatty alcohols which are liquid at room temperature and contain a branched and/or unsaturated carbon-based chain having from 18 to 20 carbon atoms, triglycerides of glycerol and of $C_{14}$-$C_{22}$ fatty acids and mixtures thereof. Preferably, the composition according to the invention comprises at least one polar oil chosen from octyldodecanol, oleyl alcohol, castor oil, camelina oil and mixtures thereof; even better still, the composition according to the present invention comprises at least one oil chosen from octyldodecanol, oleyl alcohol, castor oil and mixtures thereof.

In a second embodiment, the composition according to the invention comprises at least two polar oils as defined above, different from one another; in particular, at least one first polar oil chosen from fatty alcohols which are liquid at room temperature and contain a branched and/or unsaturated carbon-based chain having from 18 to 20 carbon atoms, and at least one second polar oil chosen from triglycerides of glycerol and of $C_{14}$-$C_{22}$ fatty acids. Preferably, the composition according to the invention comprises at least two polar oils, including at least one first polar oil chosen from octyldodecanol, oleyl alcohol, and mixtures thereof, and at least one second polar oil chosen from castor oil, camelina oil, and mixtures thereof; even better still, at least two polar oils, including at least one first polar oil chosen from octyldodecanol, oleyl alcohol, and mixtures thereof, and a second polar oil which is castor oil.

Preferably, said "at least one first polar oil" is present in the composition in a concentration of between 25% and 50% by weight relative to the total weight of the composition, and said "at least one second polar oil" is present in the composition in a concentration of between 5% and 15% by weight relative to the total weight of the composition.

Preferentially, said "at least one first polar oil" is present in the composition in a concentration of between 35% and 45% by weight relative to the total weight of the composition, and said "at least one second polar oil" is present in the composition in a concentration of between 5% and 15% by weight relative to the total weight of the composition.

The composition according to the invention preferably comprises from 2.5% to 15% by weight of linear, branched, saturated or unsaturated $C_{18}$ fatty acids, including 0 to 1% by weight of saturated $C_{18}$ fatty acids such as stearic acid, from 2.5% to 15% by weight of monounsaturated fatty acids such as ricinoleic and/or oleic acids, and/or from 0.1% to 11% by weight of polyunsaturated $C_{18}$ fatty acids such as linoleic and/or linolenic acids, relative to the total weight of said composition; and/or from 25% to 50% by weight of at least one fatty alcohol which is liquid at room temperature and contains a branched and/or unsaturated carbon-based chain having from 18 to 20 carbon atoms, relative to the total weight of said composition.

Preferably, the composition according to the invention may comprise from 2.5% to 15% by weight of linear, branched, saturated or unsaturated $C_{18}$ fatty acids, including 0 to 1% by weight of saturated $C_{18}$ fatty acids such as stearic acid, from 2.5% to 15% by weight of monounsaturated fatty acids such as ricinoleic and/or oleic acids, and/or from 0.1% to 11% by weight of polyunsaturated $C_{18}$ fatty acids such as linoleic and/or linolenic acids, relative to the total weight of said composition; and/or from 35% to 45% by weight of at least one fatty alcohol which is liquid at room temperature and contains a branched and/or unsaturated carbon-based chain having from 18 to 20 carbon atoms, relative to the total weight of said composition.

Additional Fatty Substances

The composition according to the invention may comprise additional fatty substances different from the abovementioned polar oils and especially one or more apolar oils and/or one or more solid and/or pasty fatty substances.

For the purposes of the present invention, "apolar oil" means an oil of which the solubility parameter $\delta_a$ at 25° C. as defined above is equal to 0 $(J/cm^3)^{1/2}$.

Among the apolar oils, mention may be made, for example, of:

Non-Volatile Apolar Oils

Hydrocarbon-based oils of mineral or synthetic origin, such as, for example: linear or branched hydrocarbons of mineral or synthetic origin, such as petroleum jelly, polydecenes, hydrogenated polyisobutene such as Parleam, and squalane, and mixtures thereof, and in particular hydrogenated polyisobutene.

Volatile Apolar Oils

The volatile hydrocarbon-based oils may be chosen from hydrocarbon-based oils having from 8 to 16 carbon atoms, and especially branched $C_8$-$C_{16}$ alkanes (also referred to as isoparaffins) such as isododecane (also referred to as 2,2,4,4,6-pentamethylheptane), isodecane, isohexadecane, and for example the oils sold under the trade names Isopars® or Permethyls®; linear alkanes, for example such as n-dodecane (C12) and n-tetradecane (C14), sold by Sasol respectively under the references PARAFOL 12-97 and PARAFOL 14-97, and also the mixtures thereof, the undecane-tridecane mixture (Cétiol UT®), the n-undecane (C11) and n-tridecane (C13) mixtures obtained in examples 1 and 2 of application WO2008/155059 from Cognis, and mixtures thereof.

Preferably, the apolar oil is chosen from non-volatile apolar oils; even better still, the apolar oil is chosen from hydrocarbon-based oils of mineral or synthetic origin, in particular linear or branched hydrocarbons of mineral or synthetic origin. In a preferred embodiment, the apolar oil is squalane.

Preferably, the composition according to the invention comprises less than 10% by weight of apolar oil relative to the total weight of the composition, preferentially less than 6% by weight of apolar oil, even better still less than 5% by weight of apolar oil relative to the total weight of the composition, or even the composition is free from apolar oil.

In another preferred embodiment, the composition according to the invention comprises from 1% to 10% by weight of apolar oil relative to the total weight of the composition, preferentially from 2% to 6% by weight of apolar oil, even better still from 3% to 5% by weight of apolar oil relative to the total weight of the composition.

The other fatty substances which may be present in the composition according to the invention are especially solid and/or pasty fatty substances.

"Solid fatty substance" is intended to mean any fatty substance that is in solid form at room temperature (25° C.) and at atmospheric pressure.

"Pasty fatty substance" is intended to denote a lipophilic fatty compound that undergoes a reversible solid/liquid change in state, having an anisotropic crystal organization in the solid state, and comprising, at a temperature of 23° C., a liquid fraction and a solid fraction. In other words, the starting melting point of the pasty fatty substance may be less than 23° C. The liquid fraction of the pasty fatty substance measured at 23° C. may represent 9% to 97% by weight of the pasty fatty substance. This fraction that is liquid at 23° C. preferably represents between 15 and 85% and more preferably between 40 and 85% by weight.

The melting point corresponds to the temperature of the most endothermic peak observed on thermal analysis (DSC) as described in standard ISO 11357-3; 1999. The melting point of a pasty fatty substance may be measured using a differential scanning calorimeter (DSC), for example the calorimeter sold under the name MDSC 2920 by TA Instruments.

According to a particular embodiment of the invention, the composition according to the invention comprises less than 3% by weight of solid and/or pasty fatty substances, preferentially less than 2% by weight of solid and/or pasty fatty substances, even better still less than 1% by weight of solid and/or pasty fatty substances relative to the total weight of the composition. Preferably, the composition comprises from 0 to 3% by weight of solid and/or pasty fatty substances, preferentially from 0 to 2% by weight of solid and/or pasty fatty substances, even better still from 0 to 1% by weight of solid and/or pasty fatty substances.

According to a particularly preferred embodiment, the composition is free from solid and/or pasty fatty substances.

$C_2$-$C_6$ Monoalcohol

The composition according to the invention comprises from 10% to 45% by weight of at least one $C_2$-$C_6$ aliphatic monoalcohol, preferably from 12% to 30% by weight, preferably from 13% to 23% by weight of at least one $C_2$-$C_6$ aliphatic monoalcohol.

Preferentially, said aliphatic monoalcohol comprises from 2 to 4 carbon atoms.

The term "aliphatic monoalcohol" means any linear or branched, saturated alkane compound bearing only one hydroxyl (OH) function.

The aliphatic monoalcohol(s) present in the compositions of the invention may be chosen from ethanol, propanol, butanol, isopropanol and isobutanol, or mixtures thereof. More particularly, ethanol will be selected.

Polyol

The composition according to the invention comprises from 0.5% to 50% by weight of at least one polyol relative to the total weight of the composition; preferably, the composition comprises from 5% to 35% by weight, even more preferentially from 10% to 30% by weight of at least one polyol, even better still from 15% to 25% by weight of at least one polyol relative to the total weight of the composition.

For the purposes of the present invention, the term "polyol" should be understood as meaning any organic molecule comprising at least two free hydroxyl groups.

A polyol that is suitable for use in the invention may be a compound of linear, branched or cyclic, saturated or unsaturated alkyl type, bearing at least two —OH functions on the alkyl chain. Preferably, a polyol that may be used in the composition according to the invention is a compound of linear alkyl type bearing at least two -OH functions, preferably 2 to 3 —OH functions, on the alkyl chain.

The polyols that are advantageously suitable for formulating the cosmetic compositions according to the present invention are those especially having from 2 to 16 carbon atoms and preferably 3 to 8 carbon atoms.

The polyols that may be used according to the present invention are chosen from linear polyols having from 3 to 8 carbon atoms; mention may be made especially of:
  diols such as propylene glycol, butylene glycol and pentylene glycol; and
  triols, such as glycerol (glycerin),
and mixtures thereof.

According to a particular embodiment, the linear polyol having from 3 to 8 carbon atoms is chosen from butylene glycol, propylene glycol, pentylene glycol and mixtures thereof.

According to a preferred mode, the polyol is pentylene glycol.

Hydrophilic Active Agent(s)

The composition comprises at least one hydrophilic active agent.

"Hydrophilic active agent" is intended to mean a water-soluble or water-dispersible active agent, capable of forming hydrogen bonds.

As hydrophilic active agents, mention may be made, for example, of moisturizers; depigmenting agents; desquamating agents; anti-ageing agents; mattifying agents; cicatrizing agents; antibacterial agents; and mixtures thereof.

The composition according to the invention may comprises from 0.01% to 20% by weight of at least one hydrophilic active agent, preferentially from 0.1% to 10% by weight of at least one hydrophilic active agent relative to the total weight of the composition.

Preferably, the said hydrophilic active agent is chosen from C-glycosides, salicylic acid, salicylic acid derivatives and mixtures thereof.

In a first embodiment, the composition according to the invention may comprise at least one hydrophilic active agent chosen from C-glycosides of the following general formula (I):

in which:
  R denotes an unsubstituted linear $C_1$-$C_4$ and especially $C_1$-$C_2$ alkyl radical, in particular methyl;
  S represents a monosaccharide chosen from D-glucose, D-xylose, N-acetyl-D-glucosamine and L-fucose, and in particular D-xylose;
  X represents a group chosen from —CO—, —CH(OH)— and —CH(NH$_2$)— and preferentially a —CH(OH)— group;
and also the cosmetically acceptable salts thereof, solvates thereof such as hydrates, and optical isomers thereof.

As non-limiting illustrations of C-glycoside derivatives of formula (I) that are more particularly suitable for the invention, mention may especially be made of the following compounds:
  C-beta-D-xylopyranoside-n-propan-2-one;
  C-alpha-D-xylopyranoside-n-propan-2-one;
  C-beta-D-xylopyranoside-2-hydroxypropane;
  C-alpha-D-xylopyranoside-2-hydroxypropane;
  1-(C-beta-D-glucopyranosyl)-2-hydroxypropane;
  1-(C-alpha-D-glucopyranosyl)-2-hydroxypropane;
  1-(C-beta-D-glucopyranosyl)-2-aminopropane;
  1-(C-alpha-D-glucopyranosyl)-2-aminopropane;
  3'-(acetamido-C-beta-D-glucopyranosyl)propan-2'-one;
  3'-(acetamido-C-alpha-D-glucopyranosyl)propan-2'-one;
  1-(acetamido-C-beta-D-glucopyranosyl)-2-hydroxypropane;
  1-(acetamido-C-beta-D-glucopyranosyl)-2-aminopropane;
  and also the cosmetically acceptable salts thereof, solvates thereof such as hydrates, and optical isomers thereof.

According to a particular embodiment, use is made of C-beta-D-xylopyranoside-2-hydroxypropane or C-alpha-D-xylopyranoside-2-hydroxypropane, and better still C-beta-D-xylopyranoside-2-hydroxypropane.

According to a particular embodiment, a C-glycoside of formula (I) that is suitable for the invention may advantageously be C-beta-D-xylopyranoside-2-hydroxypropane, the INCI name of which is HYDROXYPROPYL TETRAHYDROPYRANTRIOL, sold especially under the name MEXORYL SBB® or MEXORYL SCN® by CHIMEX. The salts of the C-glycosides of formula (I) that are suitable for the invention may comprise conventional physiologically acceptable salts of these compounds, such as those formed from organic or inorganic acids. Examples that may be mentioned include the salts of mineral acids, such as sulfuric acid, hydrochloric acid, hydrobromic acid, hydriodic acid, phosphoric acid and boric acid. Mention may also be made of the salts of organic acids, which may comprise one or more carboxylic, sulfonic or phosphonic acid groups. They may be linear, branched or cyclic aliphatic acids, or alternatively aromatic acids. These acids may also comprise one or more heteroatoms chosen from O and N, for example in the form of hydroxyl groups. Mention may especially be made of propionic acid, acetic acid, terephthalic acid, citric acid and tartaric acid.

The solvates that are acceptable for the compounds described above comprise conventional solvates such as those formed during the final step of preparation of said compounds due to the presence of solvents. Examples that may be mentioned include solvates due to the presence of water or of linear or branched alcohols, such as ethanol or isopropanol.

The C-glycosides (I) are known from the document WO 02/051828.

According to one embodiment, the composition according to the invention comprises a C-glycoside in an amount of between 0.05% and 10% by weight of active material (C-glycoside) relative to the total weight of the composition, in particular between 0.5% and 5% by weight of active material relative to the total weight of the composition and more particularly between 1% and 4% by weight of active material relative to the total weight of the composition.

In another particular embodiment, the composition according to the invention may comprise at least one hydrophilic active agent chosen from salicylic acid and salicylic acid derivatives, in particular of formula (II) below:

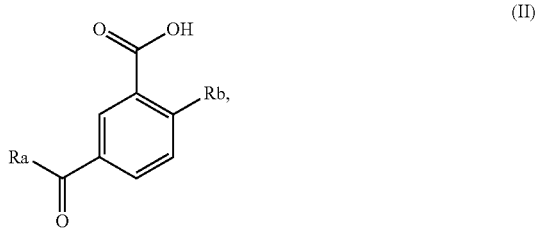

(II)

in which:
the radical Ra denotes:
a linear, branched or cyclic, saturated aliphatic chain containing from 2 to 22 carbon atoms;
an unsaturated chain containing from 2 to 22 carbon atoms, containing one or more double bonds which may be conjugated;
an aromatic nucleus bonded to the carbonyl radical directly or by means of saturated or unsaturated aliphatic chains containing from 2 to 7 carbon atoms;
it being possible for said groups to be substituted with one or more identical or different substituents chosen from:
(a) halogen atoms,
(b) the trifluoromethyl group,
(c) hydroxyl groups in free form or in a form esterified with an acid containing from 1 to 6 carbon atoms, or
(d) a carboxyl function in free form or in a form esterified with a lower alcohol containing from 1 to 6 carbon atoms;
Rb is a hydroxyl group;
and also salts thereof derived from an inorganic or organic base.

According to one embodiment, the radical Ra denotes:
a linear, branched or cyclic, saturated aliphatic chain containing from 3 to 11 carbon atoms; or
an unsaturated chain containing from 3 to 17 carbon atoms and comprising one or more conjugated or non-conjugated double bonds;
it being possible for said hydrocarbon-based chains to be substituted with one or more identical or different substituents chosen from:
(a) halogen atoms;
(b) the trifluoromethyl group;
(c) hydroxyl groups in free form or in a form esterified with an acid containing from 1 to 6 carbon atoms; or
(d) a carboxyl function in free form or in a form esterified with a lower alcohol containing from 1 to 6 carbon atoms;
and also salts thereof obtained by salification with an inorganic or organic base. The compounds that are more particularly preferred are those in which the radical Ra is a $C_3$-$C_{11}$ alkyl group. Among the compounds of formula (II) that are particularly preferred, mention may be made of: 5-n-octanoylsalicylic acid (or capryloylsalicylic acid); 5-n-decanoylsalicylic acid; 5-n-dodecanoylsalicylic acid; 5-n-heptyloxysalicylic acid, and the corresponding salts thereof. The salicylic acid compound is advantageously chosen from salicylic acid and 5-n-octanoylsalicylic acid. 5-n-Octanoylsalicylic acid will more particularly be used. 5-n-Octanoylsalicyliic acid (or capryloylsalicylic acid) is provided under the name Mexoryl SAB® by the company Chimex.

Examples of inorganic bases that may be mentioned include alkali metal or alkaline-earth metal hydroxides, for instance sodium hydroxide, potassium hydroxide or aqueous ammonia. Among the organic bases that may be mentioned are amines and alkanolamines. Quaternary salts, for instance those described in patent FR 2 607 498, are particularly advantageous. The compounds of formula (II) that may be used according to the invention are described in patents U.S. Pat. No. 6,159,479, U.S. Pat. No. 5,558,871, FR 2 581 542, FR 2 607 498, U.S. Pat. No. 4,767,750, EP 378 936, U.S. Pat. No. 5,267,407, U.S. Pat. No. 5,667,789, U.S. Pat. No. 5,580,549 and EP A-570 230.

According to one embodiment, the salicylic acid or the salicylic acid compound of formula (II) as previously described is present in the composition according to the invention in an amount ranging from about 0.1% to about 5% by weight of active material (salicylic acid or derivative), relative to the total weight of the composition, preferably ranging from about 0.1% to about 1% by weight of active material, for example about 0.3% by weight of active material.

In a known manner, all the compositions of the invention may comprise one or more of the adjuvants that are common in the fields of cosmetics and dermatology: lipophilic gelling agents and/or thickeners; moisturizers; emollients; lipophilic active agents; free-radical scavengers; sequestrants; antioxidants; essential oils; fragrances; film-forming agents; soluble dyes; and mixtures thereof.

The amounts of these various adjuvants are those conventionally used in the fields under consideration. In particular, these amounts vary according to the desired aim and may range, for example, from 0.01% to 20% and preferably from 0.1% to 10% by weight relative to the total weight of the composition.

Of course, those skilled in the art will take care to select the optional adjuvant(s) added to the composition according to the invention such that the advantageous properties intrinsically associated with the composition in accordance with the invention are not, or are not substantially, adversely affected by the envisioned addition.

As gelling agents and/or lipophilic thickeners, mention may be made of esters of dextrin and of fatty acids, in particular dextrin palmitates, such as, for example, those sold under the name Rheopearl TL2-OR or Rheopearl KL2-OR by Chiba Flour Milling, and under the name Rheopearl KS by Chiba Flour Milling, and dextrin myristates, such as, for example, those sold under the name Rheopearl MKL2 by Chiba Flour Milling. Mention may also be made of triesters of fatty acids and of mono- or polyglycerol, such as glyceryl tri(hydroxystearate) (INCI name: TRIHYDROX-YSTEARIN) such as, for example, that sold by ELEMENTIS under the name THIXCIN R or that sold by BYK ADDITIVES & INSTRUMENTS under the name RHEOCIN; modified clays such as hectorite and derivatives thereof, such as the products sold under the Bentone names.

Preferentially, the composition comprises less than 3% by weight of lipophilic thickeners and/or gelling agents, preferably less than 2% by weight of lipophilic thickeners and/or gelling agents relative to the total weight of the composition, better still less than 1% by weight of lipophilic thickeners and/or gelling agents relative to the total weight of the composition. In one particular embodiment, the composition is free from lipophilic thickeners and/or gelling agents.

Additional Active Agents

The composition according to the invention may also comprise additional active agents different from the above-mentioned hydrophilic active agents.

The amounts of these various active agents are those conventionally used in the fields under consideration. In particular, these amounts vary according to the desired aim and may range, for example, from 0.01% to 20% and preferably from 0.1% to 10% by weight relative to the total weight of the composition.

Of course, those skilled in the art will take care to select the optional active agent(s) added to the composition according to the invention such that the advantageous properties intrinsically associated with the composition in accordance with the invention are not, or are not substantially, adversely affected by the envisioned addition.

In a particular embodiment, the composition according to the invention does not comprise fluconazole.

The composition may also comprise one or more UV screening agents, in particular organic screening agents, especially liposoluble organic screening agents.

According to a particular embodiment, the composition in accordance with the invention comprises less than 2% by weight of fillers relative to the total weight of the composition; preferably, the composition according to the invention comprises from 0 to 2% by weight of fillers relative to the total weight of the composition; even better still, the composition according to the invention is free from fillers.

"Filler" should be understood as meaning colourless or white, mineral or synthetic particles of any shape, which are insoluble in the medium of the composition, irrespective of the temperature at which the composition is manufactured.

In a particular embodiment, the composition according to the invention does not comprise microspheres such as cross-linked polymethyl methacrylates (PMMA) such as, for example, those sold under the name Covabead LH 85 sold by Sensient.

Another subject of the invention is also the cosmetic use of the composition as defined above, for caring for keratin materials, in particular for caring for the skin of the body and/or of the face. The composition in accordance with the invention may especially be used as a product for cosmetic use for care, and also as fragrancing products.

Another subject of the present invention is a non-therapeutic cosmetic treatment process for caring for keratin materials such as the skin, in particular the skin of the body and/or of the face, in which a composition as defined above is applied to the skin.

The composition in accordance with the invention may be obtained in the usual manner for those skilled in the art.

The examples that follow will allow the invention to be understood more clearly, without, however, being limiting in nature. The starting materials are referred to by their chemical or INCI name. The amounts indicated are weight percentages of starting materials, unless otherwise indicated.

EXAMPLES

The compositions 1 to 3 below in accordance with the present invention were produced.

| Phase | INCI name | Composition No. 1 (composition according to the invention) % w/w | Composition No. 2 (composition according to the invention) % w/w | Composition No. 3 (composition according to the invention) % w/w |
|---|---|---|---|---|
| A1 | Arginine | 0.1 | 0.1 | 0.1 |
| | Hydroxypropyl tetrahydropyrantriol (MEXORYL SCN ® sold by CHIMEX (35% of AM*)) | 8.67 (=3.03% of AM) | 8.67 (=3.03% of AM) | 8.67 (=3.03% of AM) |
| A2 | Pentylene glycol (PENTIOL GREEN+ ® sold by MINASOLVE) | 23.35 | 24.85 | 19.85 |
| | Glycerol | 1.5 | — | — |
| A3 | Ethanol (ETHANOL S96 DENATURE BITREX/TERTIO ® by France ALCOOLS) | 15 | 15 | 20 |
| B | Octyldodecanol (EUTANOL G ® sold by BASF) | 29.88 (q.s) | 29.88 (q.s) | 33.88 (q.s) |
| | Castor oil (Crystal O ® sold by VERTELLUS) | 7.5 | 7.5 | 7.5 |
| | Oleyl alcohol (HD OCENOL 80/85 V/MB ® sold by BASF) | 10 | 10 | 10 |
| | *Camelina* oil (CAMELINA REFINED OIL C05002 ® sold by GREENTECH) | 4 | — | — |
| | Squalane (EXOLIVE ® sold by CAROI LINE COSMETICA) | — | 4 | — |

*AM: active material

Production Method
a) Carry out a pre-dispersion of the phase A1 under magnetic stirring or deflocculator for 25 minutes at 50° C.-55° C. until a perfectly homogeneous and clear mixture is obtained, then add the phase A2 until a perfectly homogeneous and clear mixture is obtained.
b) Cool the mixture and add the phase A3 until a perfectly homogeneous and clear mixture is obtained.
c) Add the phase B until a perfectly homogeneous and clear mixture is obtained.

A) Evaluation of the Stability of Compositions 1 to 3

|  | Organoleptic characteristics | | | |
|---|---|---|---|---|
|  | at 24 h | 2 months at 4° C. | 2 months at 45° C. | Cyclic study (10 cycles of 24 h) |
| Appearance | Homogeneous, clear, liquid oil | Homogeneous, clear, liquid oil | Homogeneous, clear, liquid oil | Homogeneous, clear, liquid oil |
| Colour | Very light yellow | Very light yellow | Very light yellow | Very light yellow |
| Odour | Fragranced | Fragranced | Fragranced | Fragranced |

The following organoleptic characteristics were evaluated 24 h after the production of the compositions 1 to 3 above; in particular, the following were measured:
  appearance: homogeneity, clarity, liquidity, fluidity.
  colour: hue, and optionally intensity level thereof (light or dark).
  odour: stable, constant odour.

The same organoleptic characteristics were evaluated after 2 months at 4° C. and 2 months at 45° C. The results obtained show that the compositions 1 to 3 according to the invention remain stable for 2 months at a temperature of 4° C. and 45° C., since the organoleptic characteristics (appearance, colour, odour) observed at T24 h remain stable for 2 months at a temperature of 4° C. and 45° C.

In addition, the cyclic study corresponding to 10 cycles of 24 h (one cycle corresponding to conserving the composition for 6 h at 20° C., then 6 h decreasing down to −20° C., then 6 h at −20° C., and finally 6 h rising back up to 20° C.) shows that the compositions 1 to 3 according to the invention are stable, since the organoleptic characteristics observed after this study do not exhibit any variations.

B) Sensory Evaluation

The sensory nature of the compositions 1 to 3 above was evaluated according to two protocols as described below.

a) Evaluation of the Skin Finish with a Reconstructed Skin SKIN FX®

The sensory nature of the above composition was evaluated by a panel of 3 people.

A layer of 35 µl of the above composition was applied onto a neutral support of Skin FX type (silicone-based support 80 mm in diameter, covered with a polyurethane film). This layer, especially in terms of thickness, is similar to a layer resulting from the conventional application of a composition by a user.

The application is carried out in the following manner:
  Deposit the product on the support
  Spread the product with the fingers, making 15 rounds in 15 seconds (evaluation of smoothness)
  Wait 15 seconds
  Continue the application, making a further 15 rounds in 15 seconds (evaluation of the greasy-butteriness on the fingers and the speed of penetration)
  Wait 2 minutes
  Evaluation of the criteria below.

The following criteria were evaluated on a scale from 1 to 5 (1 corresponding to "little" and 5 corresponding to "a lot/very"):
  Smoothness on application
  Greasy feel on the fingers during application
  Shiny finish 2.45 minutes*
  Tacky finish 2.45 minutes*
  Film-forming finish 2.45 minutes*

*15 seconds of application, then 15 seconds of drying naturally, then a further 15 seconds of application then 2 minutes of drying naturally

| Evaluation criteria | Composition no. 1 | Composition no. 2 | Composition no. 3 |
|---|---|---|---|
| Smoothness on application | 4.50/5 | 4.50/5 | 4.25/5 |
| Greasy feel on the fingers during application | 2.50/5 | 2.50/5 | 2.40/5 |
| Shiny finish after 2.45 minutes | 2.50/5 | 2.50/5 | 2.50/5 |
| Tacky finish after 2.45 minutes | 1.50/5 | 1.75/5 | 1.50/5 |
| Film-forming finish after 2.45 minutes | 2.50/5 | 2.50/5 | 2.25/5 |

The values indicated in the table above correspond to a mean produced from 3 people. The acceptable standard deviation is +/−1.

The above results show that the compositions 1 to 3 have a weakly greasy feel on the fingers during application, and also a weakly shiny, tacky and film-forming finish after application.

b) Sensory Evaluation on Facial Skin by a Panel of Experts

The sensory nature of the above compositions 1 to 3 was evaluated by a panel of 16 experts.

An amount of 0.15 ml of each of the compositions 1 to 3 was applied to a half face. This evaluation was carried out blind with 2 repetitions.

The following criteria were evaluated on a scale of 0 to 15 (from the minimum to the maximum):

| Evaluation criteria | Composition no. 1 | Composition no. 2 | Composition no. 3 |
|---|---|---|---|
| Speed of penetration during application | 8.59/15 | 8.21/15 | 9.20/15 |
| Greasy residue on the fingers during application | 5.44/15 | 5.67/15 | 5.40/15 |
| Spread during application | 6.69/15 | 6.60/15 | 6.80/15 |
| Greasy finish 1 min after application | 8.28/15 | 8.36/15 | 7.64/15 |
| Tacky finish 1 min after application | 7.29/15 | 7.16/15 | 6.65/15 |
| Shiny finish 1 min after application | 7.62/15 | 7.59/15 | 6.88/15 |
| Film-forming finish 1 min after application | 1.50/15 | 1.59/15 | 1.77/15 |
| Greasy finish 3 min after application | 6.80/15 | 7.19/15 | 6.79/15 |
| Tacky finish 3 min after application | 6.02/15 | 6.08/15 | 5.92/15 |
| Shiny finish 3 min after application | 6.77/15 | 6.68/15 | 6.13/15 |
| Film-forming finish 3 min after application | 1.54/15 | 1.64/15 | 1.76/15 |

C) Evaluation on Skin Explant of the Effectiveness of a Hydrophilic Active Agent, in Particular of a C-glycoside Derivative This evaluation made it possible to demonstrate that the composition according to the invention does indeed make it possible to deliver hydrophilic ingredients, in particular C-glycoside derivatives such as hydroxypropyl tetrahydropyrantriol.

The formulas below were produced:

| Phase | INCI name | Composition No. 1 (according to the invention) % w/w | Composition No. 4 (outside the invention) % w/w |
|---|---|---|---|
| A1 | Arginine | 0.1 | — |
|  | Hydroxypropyl tetrahydropyrantriol (MEXORYL SCN sold by CHIMEX (35% of AM*)) | 8.67 (=3.03% of AM) | — |
| A2 | Pentylene glycol (PENTIOL GREEN+ sold by MINASOLVE) | 23.35 | 23.35 |
|  | Glycerol | 1.5 | 1.5 |
| A3 | Ethanol | 15 | 15 |
| B | Octyldodecanol (EUTANOL G sold by BASF) | 29.88 (q.s) | 38.58 (q.s) |
|  | Castor oil (Crystal O sold by VERTELLUS) | 7.5 | 7.5 |
|  | Oleyl alcohol (HD OCENOL 80/85 V/MB sold by BASF) | 10 | 10 |
|  | *Camelina* oil (*CAMELINA* REFINED OIL C05002 sold by GREENTECH) | 4 | 4 |

Production Method a) Carry out a pre-dispersion of the phase A1 under magnetic stirring or deflocculator for 25 minutes at 50° C.-55° C. until a perfectly homogeneous and clear mixture is obtained, then add the phase A2 until a perfectly homogeneous and clear mixture is obtained.

b) Cool the mixture and add the phase A3 until a perfectly homogeneous and clear mixture is obtained.

c) Add the phase B until a perfectly homogeneous and clear mixture is obtained.

Thus, each of the compositions 1 and 4 was applied to skin explants which had been kept alive. The neosynthesis of glycosaminoglycans (GAG) sulfated by incorporation of [35S]-sulfate was monitored. It is a sign of the biological effectiveness of the hydroxypropyl tetrahydropyrantriol and thus demonstrates that the active agent was delivered into the skin. The biological model used corresponds to ex vivo skin explants originating from surgery.

Culture conditions: 37° C., 5% $CO_2$.

Culture medium: Maintenance medium (supplier: BIO-alternatives)

The skin explants are placed in 24-well plates (1 punch/well) then treated or untreated (control) topically with the formulas (pure application at 20 mg/cm²). The explants were then incubated for 72 hours and the radioactive marker [35S]-sulfate (12 µCi/well) was added for the final 48 hours of incubation.

The control condition was performed with n=7 and the experimental conditions for the compounds with n=4.

At the end of incubation, the culture supernatants were collected and frozen at −20° C. to measure the incorporation of [35S]-sulfate into the neosynthesized GAGs released into the medium.

TABLE

| Treatment | | Culture supernatant | | | | | |
|---|---|---|---|---|---|---|---|
| Compounds Tested | Concentration (Topical application) | [$^{35}$S]-Sulfate (cpm) | mean (cpm) | SEM (cpm) | % Control | SEM (%) | p[(1)] |
| Control | — | 3828 5389 6917 6354 6426 7671 | 6098 | 547 | 100 | 9 | — |
| Composition no 4 not according to the invention | Pure (20 mg/cm³) | 6480 7105 6221 | 6602 | 262 | 108 | 4 | no |
| Composition no 1 according to the invention | Pure (20 mg/cm³) | 43776 72723 42183 | 52894 | 9925 | 867 | 163 | ... |

[(1)] statistical significance threshold
ns: >0.05. not significant
*: 0.01 to 0.05. significant
**: 0.001 to 0.01. very significant
***: <0.001. extremely significant Under the experimental conditions, the composition no.1 according to the invention, containing hydroxypropyl tetrahydropyrantriol tested pure and applied topically, clearly and significantly stimulated the incorporation of [35S]-sulfate into the fraction of GAGs released into the culture supernatants (+867% relative to the untreated control skin). The composition no.4 outside of the invention does not alter the neosynthesis of GAGs. Indeed, the carrier did not significantly alter the incorporation of [35S]-sulfate of the sulfated GAGs released into the culture media.

Thus, the composition no. 1 according to the invention does indeed make it possible to deliver hydroxypropyl tetrahydropyrantriol, a hydrophilic active agent, during application to keratin materials, and thereby to induce the synthesis of GAGs and hence to enable a good effectiveness of the active agent in the treatment of the signs of skin ageing.

The invention claimed is:

1. A cosmetic composition, which comprises from 30% to 89% by weight relative to the total weight of the composition of at least two polar oils wherein at least one first polar oil is chosen from fatty alcohols which are liquid at room temperature and contain a branched and/or unsaturated carbon-based chain having from 18 to 20 carbon atoms, and at least one second polar oil is chosen from triglycerides of glycerol and of $C_{14}$-$C_{22}$ fatty acids, from 10% to 45% by weight of ethanol relative to the total weight of the composition, and from 0.5% to 50% by weight of at least one polyol chosen from propylene glycol, butylene glycol, pentylene glycol, glycerol and mixtures thereof relative to the total weight of the composition, and at least one hydrophilic active agent, said composition comprising less than 7% by weight of water relative to the total weight of the composition, wherein the composition comprises from 0% to 3% by weight of solid and/or pasty fatty substances relative to the total weight of the composition and less than 5% by weight of surfactant relative to the total weight of the composition, and wherein the hydrophilic active agent is chosen from C-glycosides, salicylic acid, salicylic acid derivatives and mixtures thereof.

2. The composition according to claim 1, comprising from 40% to 60% by weight of at least one polar oil relative to the total weight of the composition.

3. The composition according to claim 1, wherein said at least one first polar oil is present in a concentration of between 25% and 50% by weight relative to the total weight of the composition, and said at least one second polar oil is present in a concentration of between 5% and 15% by weight relative to the total weight of the composition.

4. The composition according to claim 1, comprising from 12% to 30% by weight of ethanol relative to the total weight of the composition.

5. The composition according to claim 1 comprising from 5% to 35% by weight of at least one polyol relative to the total weight of the composition.

6. The composition according to claim 1, wherein the hydrophilic active agent comprises a C-glycoside.

7. The composition according to claim 6, wherein the C-glycoside is chosen from the compounds of following formula (I):

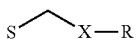

in which:
R denotes a C1-C4, especially C1-C2 unsubstituted linear alkyl radical, in particular methyl;
S represents a monosaccharide chosen from D-glucose, D-xylose, N-acetyl-D-glucosamine and L-fucose;
X represents a group chosen from —CO—, —CH(OH)—, —CH(NH₂)—, and the cosmetically acceptable salts thereof, solvates thereof and optical isomers thereof.

8. The composition according to claim 6, wherein the C-glycosides of formula (I) are chosen from C-beta-D-xylopyranoside-n-propan-2-one, C-alpha-D-xylopyranoside-n-propan-2-one, C-beta-D-xylopyranoside-2-hydroxypropane, C-alpha-D-xylopyranoside-2-hydroxypropane, 1-(C-beta-D-glucopyranosyl)-2-hydroxypropane, 1-(C-alpha-D-glucopyranosyl)-2-hydroxypropane, 1-(C-beta-D-glucopyranosyl)-2-aminopropane, 1-(C-alpha-D-glucopyranosyl)-2-aminopropane, 3'-(acetamido-C-beta-D-glucopyranosyl)propan-2'-one, 3'-(acetamido-C-alpha-D-glucopyranosyl)propan-2'-one, 1-(acetamido-C-beta-D-glucopyranosyl)-2-hydroxypropane, 1-(acetamido-C-beta-D-glucopyranosyl)-2-aminopropane, and the cosmetically acceptable salts thereof, solvates thereof and optical isomers thereof.

9. The composition according to claim 6, wherein the C-glycoside of formula (I) is C-beta-D-xylopyranoside-2-hydroxypropane or C-alpha-D-xylopyranoside-2-hydroxypropane.

10. The composition according to claim 6, wherein the C-glycoside(s) of formula (I) are present in an amount of active material of between 0.05% and 10% by weight relative to the total weight of the composition.

11. The composition according to claim 1, characterized in that it is not in the form of an emulsion.

12. The composition according to claim 1, which comprises less than 6% by weight of water relative to the total weight of the composition.

13. A process for the cosmetic treatment of keratin materials comprising the topical application of the composition to said keratin materials as claimed in claim 1.

14. A process for caring for the skin of the body and/or of the face comprising the topical application of the composition to said skin as claimed in claim 1.

15. The composition according to claim 12, which comprises less than 1% by weight of surfactant relative to the total weight of the composition and 0 to 1% by weight of solid and/or pasty fatty substances relative to the total weight of the composition.

16. The composition according to claim 1, which has a viscosity of less than 1.07 Pa.s.

* * * * *